United States Patent
Law et al.

(10) Patent No.: US 6,696,209 B2
(45) Date of Patent: Feb. 24, 2004

(54) ELECTROPHOTOGRAPHIC ORGANOPHOTORECEPTORS WITH NOVEL CHARGE TRANSPORT COMPOUNDS

(75) Inventors: Kam W. Law, Woodbury, MN (US); Nusrallah Jubran, St. Paul, MN (US); Zbigniew Tokarski, Woodbury, MN (US); Alan R. Katrizky, Gainesville, FL (US); Ritu Jain, Gainesville, FL (US); Anatoily Vakulenko, Gainesville, FL (US)

(73) Assignee: Samsung Electronics Co. Ltd., Suwon (KR)

( * ) Notice: Subject to any disclaimer, the term of this patent is extended or adjusted under 35 U.S.C. 154(b) by 0 days.

(21) Appl. No.: 10/289,233

(22) Filed: Nov. 6, 2002

(65) Prior Publication Data

US 2003/0138712 A1 Jul. 24, 2003

Related U.S. Application Data

(60) Provisional application No. 60/336,999, filed on Nov. 9, 2001.

(51) Int. Cl.⁷ ............... G03G 5/047; C07D 209/82
(52) U.S. Cl. ............... 430/58.35; 430/72; 564/310
(58) Field of Search ............... 430/58.35, 72; 560/34, 13; 564/310

(56) References Cited

U.S. PATENT DOCUMENTS

| | | | |
|---|---|---|---|
| 4,297,426 A | 10/1981 | Sakai et al. | 430/59 |
| 4,415,640 A | 11/1983 | Goto et al. | 430/59 |
| 4,786,571 A | 11/1988 | Ueda | 430/59 |
| 4,869,983 A * | 9/1989 | Bender et al. | 430/58 |
| 4,957,838 A | 9/1990 | Aruga et al. | 430/59 |
| 5,128,227 A | 7/1992 | Monbaliu et al. | 430/59 |
| 5,274,116 A | 12/1993 | Martin et al. | 548/465 |
| 5,393,627 A | 2/1995 | Nakamura et al. | 430/59 |
| 5,932,384 A | 8/1999 | Mitsumori et al. | 430/59 |
| 6,001,522 A | 12/1999 | Woo et al. | 430/65 |
| 6,004,708 A | 12/1999 | Bellino et al. | 430/58.45 |
| 6,020,096 A | 2/2000 | Fuller et al. | 430/58.35 |
| 6,030,734 A | 2/2000 | Mitsumori | 430/58.8 |
| 6,066,426 A | 5/2000 | Mott et al. | 430/58.2 |
| 6,099,996 A | 8/2000 | Yanus et al. | 430/58.8 |
| 6,140,004 A | 10/2000 | Mott et al. | 430/132 |
| 6,214,503 B1 | 4/2001 | Gaidelis et al. | 430/58.45 |
| 6,232,025 B1 * | 5/2001 | Srinivasan | 430/58.4 |
| 6,340,548 B1 | 1/2002 | Jubran et al. | 430/58.45 |

* cited by examiner

*Primary Examiner*—John Goodrow
(74) *Attorney, Agent, or Firm*—Mark A. Litman & Assoc. P.A.

(57) ABSTRACT

An organophotoreceptor that includes:

(a) a charge transport compound having the formula

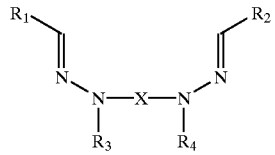

where
$R_1$ and $R_2$ are, independently, a fluorenyl group;
$R_3$ and $R_4$ are, independently, hydrogen, an alkyl group, an aryl group, or a heterocyclic group; and
X is a sulfonyldiphenylene group;

(b) a charge generating compound; and
(c) an electrically conductive substrate.

12 Claims, No Drawings

ELECTROPHOTOGRAPHIC ORGANOPHOTORECEPTORS WITH NOVEL CHARGE TRANSPORT COMPOUNDS

This application claims the benefit of Provisional Serial No. 60/336,999, filed Nov. 9, 2001.

BACKGROUND OF THE INVENTION

1. Field of the Invention

This invention relates to organophotoreceptors suitable for use in electrophotography and, more specifically, to flexible organophotoreceptors having novel charge transport compounds comprising bis(fluorenyl)-1,1'-(sulfonyldi-4,1-phenylene)bis-hydrazones.

2. Background of the Art

In electrophotography, an organophotoreceptor in the form of a plate, a flexible belt, a disk, a rigid drum, or a sheet around a rigid or compliant drum having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas, thereby forming a pattern of charged and uncharged areas (referred to as latent image). A liquid toner or solid toner is then provided in the vicinity of the latent image, and the toner particles depositing in either the charged or uncharged areas to create a toned image on the surface of the photoconductive layer. The resulting visible toner image can be transferred to a suitable receiving surface such as paper, or the photoconductive layer can operate as a permanent receptor for the image. The imaging process can be repeated many times.

Both single layer and multilayer photoconductive elements have been used. In the single layer embodiment, a charge transport material and charge generating material are combined with a polymeric binder and then deposited on an electrically conductive substrate. In the multilayer embodiment, the charge transport material and charge generating material are in the form of separate layers, each of which can optionally be combined with a polymeric binder and deposited on the electrically conductive substrate. Two arrangements are possible. In one arrangement (the "dual layer" arrangement), the charge generating layer is deposited on the electrically conductive substrate and the charge transport layer is deposited on top of the charge generating layer. In an alternate arrangement (the "inverted dual layer" arrangement), the order of the charge transport layer and charge generating layer is reversed.

In both the single and multilayer photoconductive elements, the purpose of the charge generating material is to generate charge carriers (i.e., holes or electrons) upon exposure to light. The purpose of the charge transport material is to accept these charge carriers and transport them through the charge transport layer in order to discharge a surface charge on the photoconductive element.

To produce high quality images, particularly after multiple cycles, it is desirable for the charge transport material to form a homogeneous solution (usually a solid-in-solid, or solid state solution) with the polymeric binder and remain in solution. In addition, it is desirable to maximize the amount of charge which the charge transport material can accept (indicated by a parameter known as the acceptance voltage or "$V_{acc}$"), and to minimize retention of that charge upon discharge (indicated by a parameter known as the residual voltage or "$V_{res}$").

There are many charge transport materials available for electrophotography. The most common charge transport materials are pyrazoline derivatives, fluorene derivatives, oxadiazole derivatives, stilbene derivatives, hydrazone derivatives, carbazole hydrazone derivatives, triphenylamine derivatives, julolidine hydrazone derivatives, polyvinyl carbazole, polyvinyl pyrene, or polyacenaphthylene. However, each of the above charge transport materials suffer some disadvantages. There is always a need for novel charge transport materials to meet the various requirements of electrophotography applications.

SUMMARY OF THE INVENTION

In a first aspect, the invention features an organophotoreceptor that includes:

(a) a charge transport compound having the formula

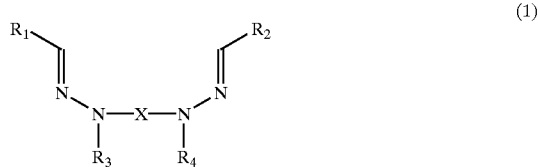

(1)

where $R_1$ and $R_2$ are, independently, a fluorenyl group;

$R_3$ and $R_4$ are, independently, hydrogen, an alkyl group, an aryl group, or a heterocyclic group; and X is a sulfonyldiphenylene group;

(b) a charge generating compound; and (c) an electrically conductive substrate.

The charge transport compound may or may not be symmetrical. Thus, for example, $R_1$ for any given "arm" of the compound may be the same or different from $R_2$ in the other "arm" of the compound. Similarly, $R_3$ for any given "arm" of the compound may be the same or different from $R_4$ in the other "arm" of the compound. In addition, the above-described formula for the charge transport compound is intended to cover isomers.

The organophotoreceptor may be provided in the form of a plate, a flexible belt, a disk, a rigid drum, or a sheet around a rigid or compliant drum. In one embodiment, the organophotoreceptor includes: (a) a charge transport layer comprising the charge transport compound and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate.

In a second aspect, the invention features an electrophotographic imaging apparatus that includes (a) a plurality of support rollers; and (b) the above-described organophotoreceptor in the form of a flexible belt threaded around the support rollers. The apparatus preferably further includes a liquid toner dispenser.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) contacting the surface with a liquid toner that includes a dispersion of colorant particles in an organic liquid to create a toned image; and (d) transferring the toned image to a substrate.

In a fourth aspect, the invention features a novel charge transport material having the formula

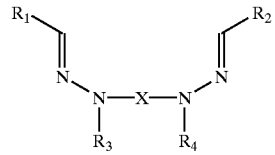

(1)

where
$R_1$ and $R_2$ are, independently, a fluorenyl group or its derivatives, as are included within the term "group";
$R_3$ and $R_4$ are, independently, hydrogen, an alkyl group, an aryl group, or a heterocyclic group; and
X is a sulfonyldiphenylene group or its derivatives, as are included within the term "group."

In one embodiment, a charge transport compound is selected in which $R_1$ and $R_2$ are, independently, a fluorenyl group, $R_3$ and $R_4$ are hydrogen, and X is a 1,1'-sulfonyldi-4,1-phenylene group. Non-limiting examples of such charge transport compound have the following structures.

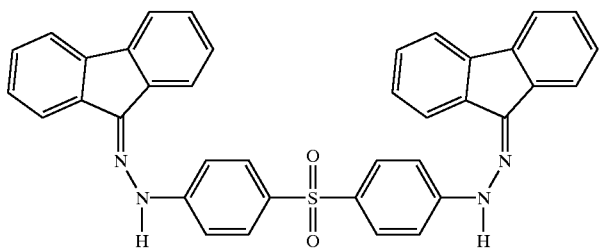

(2)

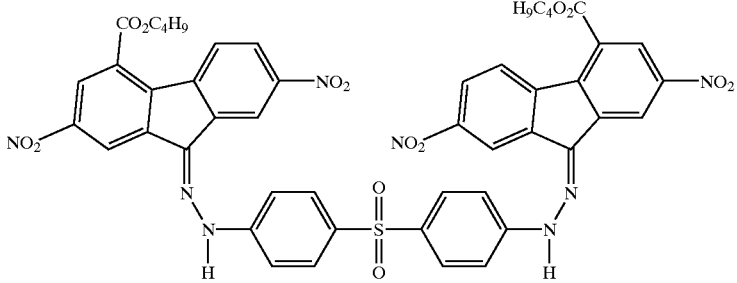

(3)

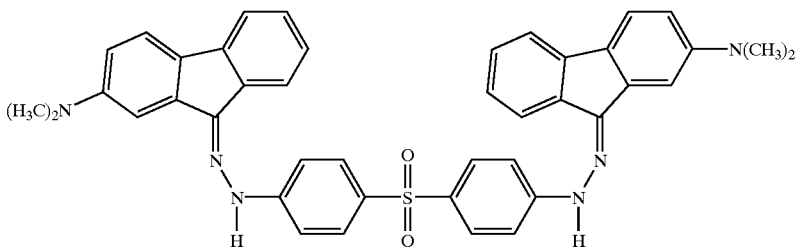

(4)

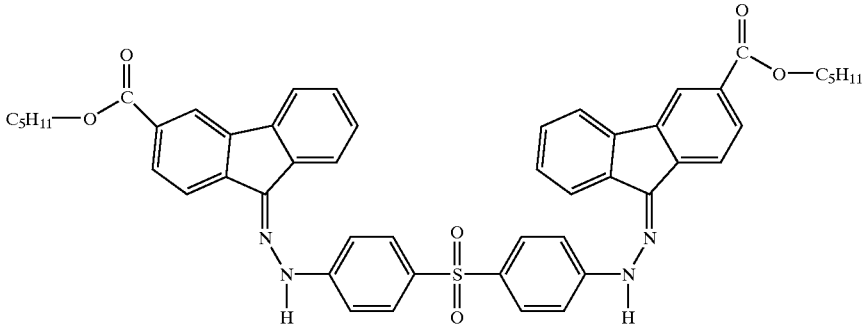

(5)

These photoreceptors can be used successfully with toners and especially liquid toners to produce high quality images. The high quality of the images is maintained after repeated cycling.

As is well understood in this technical area, a large degree of substitution is not only tolerated, but is often advisable. As a means of simplifying the discussion, the terms "nucleus", "groups" and "moiety" are used to differentiate between chemical species that allow for substitution or which may be substituted and those which do not or may not be so substituted. For example, the phrase "alkyl group" is intended to include not only pure hydrocarbon alkyl chains, such as methyl, ethyl, octyl, cyclohexyl, iso-octyl, t-butyl and the like, but also alkyl chains bearing conventional substituents known in the art, such as hydroxyl, alkoxy, phenyl, halogen (F, Cl, Br and I), cyano, nitro, amino etc. The term "nucleus" is likewise considered to allow for substitution. The phrase "alkyl moiety" on the other hand is limited to the inclusion of only pure hydrocarbon alkyl chains, such as methyl, ethyl, propyl, cyclohexyl, iso-octyl, t-butyl etc. The term "central nucleus" refers to a formula where extensive substitution is allowed on the formula, as long as substantive bonds are not removed from the structural formula. This is usually effected by removal of a hydrogen and replacement of the hydrogen with a substitutent group, without altering bond structure (e.g., removing or adding unsaturation between atoms in the nucleus).

Other features and advantages of the invention will be apparent from the following description of the preferred embodiments thereof, and from the claims.

DETAILED DESCRIPTION OF THE INVENTION

The invention features organophotoreceptors that include charge transport compounds having the formulae set forth in the Summary of the Invention above.

The organophotoreceptor may be in the form of a plate, a flexible belt, a disk, a rigid drum, or a sheet around a rigid or compliant drum, with flexible belts and rigid drums being preferred. The organophotoreceptor may include an electrically conductive substrate and a photoconductive element in the form of a single layer that includes both the charge transport compound and charge generating compound in a polymeric binder. Preferably, however, the organophotoreceptor includes an electrically conductive substrate and a photoconductive element that is a bilayer construction featuring a charge generating layer and a separate charge transport layer. The charge generating layer may be located intermediate between the electrically conductive substrate and the charge transport layer. Alternatively, the photoconductive element may be an inverted construction in which the charge transport layer is intermediate between the electrically conductive substrate and the charge generating layer.

The electrically conductive substrate may be flexible, for example in the form of a flexible web or a belt, or inflexible, for example in the form of a drum. Typically, a flexible electrically conductive substrate comprises of an insulated substrate and a thin layer of electrically conductive materials. The insulated substrate may be paper or a film forming polymer such as polyethylene terephthalate, polyimide, polysulfone, polyethylene naphthalate, polypropylene, nylon, polyester, polycarbonate, polyvinyl fluoride, polystyrene and the like. Specific examples of supporting substrates included polyethersulfone (Stabar S-100, available from ICI), polyvinyl fluoride (Tedlar™, available from E. I. DuPont de Nemours & Company), polybisphenol-A polycarbonate (Makrofol®, available from Mobay Chemical Company) and amorphous polyethylene terephthalate (Melinar™, available from ICI Americas, Inc.). The electrically conductive materials may be graphite, dispersed carbon black, iodide, conductive polymers such as polypyroles and Calgon® Conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. Preferably, the electrically conductive material is aluminum. Typically, the photoconductor substrate will have a thickness adequate to provide the required mechanical stability. For example, flexible web substrates generally have a thickness from about 0.01 to about 1 mm, while drum substrates generally have a thickness of from about 0.5 mm to about 2 mm.

The charge generating compound is a material which is capable of absorbing light to generate charge carriers, such as a dyestuff or pigment. Examples of suitable charge generating compounds include metal-free phthalocyanines, metal phthalocyanines such as titanium phthalocyanine, copper phthalocyanine, oxytitanium phthalocyanine, hydroxygallium phthalocyanine, squarylium dyes and pigments, hydroxy-substituted squarylium pigments, perylimides, polynuclear quinones available from Allied Chemical Corporation under the tradename Indofast Double Scarlet, Indofast Violet Lake B, Indofast Brilliant Scarlet and Indofast Orange, quinacridones available from DuPont under the tradename Monastral® Red, Monastral® Violet and Monastral® Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazopigments including bisazo-, trisazo- and tetrakisazopigments, polymethine dyes, dyes containing quinazoline groups, tertiary amines, amorphous selenium, selenium alloys such as selenium-tellurium, selenium-telluriumarsenic and selenium-arsenic, cadmium sulfoselenide, cadmiumselenide, cadmium sulfide, and mixtures thereof. Preferably, the charge generating compound is oxytitanium phthalocyanine, hydroxygallium phthalocyanine or a combination thereof.

Preferably, the charge generation layer comprises a binder in an amount of from about 10 to about 90 weight percent and more preferably in an amount of from about 20 to about 75 weight percent, based on the weight of the charge generation layer.

The binder is capable of dispersing or dissolving the charge transport compound (in the case of the charge transport layer) and the charge generating compound (in the case of the charge generating layer). Examples of suitable binders for both the charge generating layer and charge transport layer include polystyrene-co-butadiene, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly (hydroxyether) resins, polyhydroxystyrene resins, novolak resins, resol resins, poly(phenylglycidyl ether)-co-dicyclopentadiene, copolymers of monomers used in the above-mentioned polymers, and combinations thereof. Polycarbonate binders are particularly preferred. Examples of suitable polycarbonate binders include polycarbonate A which is derived from bisphenol-A, polycarbonate Z, which is derived from cyclohexylidene bisphenol, polycarbonate C, which is derived from methylbisphenol A, and polyestercarbonates.

The photoreceptor may include additional layers as well. Such layers are well-known and include, for example, barrier layers, release layers, adhesive layer, and sub-layer. The release layer forms the uppermost layer of the photoconductor element with the barrier layer sandwiched between the release layer and the photoconductive element. The adhesive layer locates and improves the adhesion between the barrier layer and the release layer. The sub-layer is a charge blocking layer and locates between the electrically conductive substrate and the photoconductive element. The sub-layer may also improve the adhesion between the electrically conductive substrate and the photoconductive element.

Suitable barrier layers include coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above organic binders optionally may contain small inorganic particles including by way of non-limiting examples metal oxides, metallic oxides and semimetal oxides such as fumed silica, silica, titania, alumina, zirconia, or a combination thereof The typical particle size is in the range of 0.001 to 0.5 micrometers, preferably 0.005 micrometers. A preferred barrier layer is a 1:1 mixture of methyl cellulose and methyl vinyl ether/maleic anhydride copolymer with glyoxal as a crosslinker.

The release layer topcoat may comprise any release layer composition known in the art. Preferably, the release layer is a fluorinated polymer, siloxane polymer, fluorosilicone polymer, silane, polyethylene, polypropylene, polyacrylate, or a combination thereof. More preferably, the release layers are crosslinked silicone polymers.

Typical adhesive layers include film forming polymers such as polyester, polyvinylbutyral, polyvinylpyrolidone, polyurethane, polymethyl methacrylate, poly(hydroxy amino ether) and the like. Preferably, the adhesive layer is poly(hydroxy amino ether). If such layers are utilized, they preferably have a dry thickness between about 0.01 micrometer and about 5 micrometers.

Typical sub-layers include polyvinylbutyral, organosilanes, hydrolyzable silanes, epoxy resins, polyesters, polyamides, polyurethanes, silicones and the like. Preferably, the sub-layer has a dry thickness between about 20 Angstroms and about 2,000 Angstroms.

The charge transport compounds, and photoreceptors including these compounds, are suitable for use in an imaging process with either dry or liquid toner development. Liquid toner development is generally preferred because it offers the advantages of providing higher resolution images and requiring lower energy for image fixing compared to dry toners. Examples of useful liquid toners are well-known. They typically include a colorant, a resin binder, a charge director, and a carrier liquid. A preferred resin to pigment ratio is 2:1 to 10:1, more preferably 4:1 to 8:1. Typically, the colorant, resin, and the charge director form the toner particles.

The invention will now be described further by way of the following examples.

EXAMPLES

A. Synthesis

Compound (2)

A mixture of 9-fluorenone (3.60 g, 0.02 mole, commercially available from Aldrich, Milwaukee, Wis.) and 1,1'-(sulfonyldi-4,1-phenylene)bis-hydrazine (2.78 g, 0.01 mole, commercially available from Vitas-M, Moscow, Russia; Phone: 70959395737) is refluxed in tetrahydrofuran (20 ml) for 16 hours with stirring. Upon removal of the solvent, Compound (3) is isolated and purified by recrystallization.

Compound (3)

A mixture of 2,7-dinitro-9-oxo-9H-fluorene-4-carboxylic acid butyl ester (7.4 g, 0.02 mole, commercially available from Aldrich, Milwaukee, Wis.) and 1,1'-(sulfonyldi-4,1-phenylene)bis-hydrazine (2.78 g, 0.01 mole, commercially available from Vitas-M, Moscow, Russia; Phone: 70959395737) is refluxed in tetrahydrofuran (20 ml) for 16 hours with stirring. Upon removal of the solvent, Compound (3) is isolated and purified by recrystallization.

Compound (4)

A mixture of 2-dimethylamino-9-fluorenone (4.46 g, 0.02 mole, commercially available from Aldrich, Milwaukee, Wis.) and 1,1'-(sulfonyldi-4,1-phenylene)bis-hydrazine (2.78 g, 0.01 mole, commercially available from Vitas-M, Moscow, Russia; Phone: 70959395737) is refluxed in tetrahydrofuran (20 ml) for 16 hours with stirring. Upon removal of the solvent, Compound (3) is isolated and purified by recrystallization.

Compound 5

9-Fluorenone-4-carbonyl chloride (2.44 g, 10 mmol) was refluxed overnight with an excess of n-amyl alcohol (5 mL). The solvent was evaporated and dried in vacuum to give 80% of the crude product of 9-fluorenone-4-carboxylic acid pentyl ester. The compound was recrystallized using ethyl acetate to give yellow plates; yield 74%; mp 37.9–38.1° C.; $^1$H NMR, 300 MHz, chemical shifts (ppm, CDCl3 solvent): 0.94 (t, J=7.5 Hz, 3H), 1.39–1.47 (m, 4H); 1.82 (quin., J=7.2 Hz, 2H), 4.40 (t, J=6.6 Hz, 2H), 7.31–7.36 (m, 2H), 7.40–7.52(m, 1H), 7.68–7.70 (m, 1H), 7.79–7.86 (m, 1H), 7.92 (dd, J=0.9 Hz, 1H), 8.27(d, J=7.8 Hz, 1H). C-NMR, 75 MHz, chemical shifts (ppm, CDCl3 solvent): 13.9; 22.3; 28.1; 28.3; 65.7; 124.0; 126.1; 127.0; 127.2; 128.5; 129.6; 134.3; 125.0; 135.4; 135.9; 143.1; 143.8; 166.7; 192.8.

A mixture of 1,1'-(sulfonyldi-4,1-phenylene)bis-hydrazine (2.78 g, 0.01 mole, commercially available from Vitas-M, Moscow, Russia; Phone: 70959395737), 9-fluorenone-4-carboxylic acid pentyl ester (4.74 g, 16.1 mmol) and 8–10 drops acetic acid in ethyl alcohol (120 mL) were refluxed for 48 h. After cooled to 20–25° C., the solvent was filtered. Ethyl alcohol (60 mL) was added to residue and the mixture was refluxed again for 0.5 h. The resulting mixture was cooled and precipitate was filtered, dried and dissolved in chloroform (70 mL). The mixture was filtered through celite and the filtrate was evaporated to give Compound 5 as yellow microcrystals; yield 60%; mp 131–135° C.; $^1$H NMR in CDCl3, chemical shifts (ppm): 0.91–0.95 (m, 6H); 1.40–1.41 (m, 8H), 1.75–1.80 (m, 4H); 4.31–4.40 (m, 4H); 7.08–7.34 (m, 10H); 7.57–8.31 (m, 12H); 9.00–9.04 (m, 2H)

B. Organophotoreceptor Preparation Methods

Inverted dual layer organophotoreceptor can be prepared by incorporating Compound (2) or Compound (3). A charge transport solution containing 50 wt. % of Compound (2) or Compound (3) in Polycarbonate Z binder can be prepared by combining a solution of 1.25 g of Compound (2) or Compound (3) in 8.0 g of tetrahydrofuran with 1.25 g of Polycarbonate Z in 2.50 g of toluene. The charge transport solution is then hand-coated with a Maier rod (#36) onto a 3 mil (76 micrometer) thick aluminized polyethylene terephthalate film (Melinex™ 442 polyester film from Dupont having a 1 ohm/square aluminum vapor coat) having a 0.3 micron polyester resin sub-layer (Vitel® PE-2200 from Bostik, Middletown, Mass.) and dried to form a charge transport layer having a thickness of 9 micrometers.

A dispersion can be prepared by micronising 1.35 g of oxytitanium phthalocyanine pigment (H. W. Sands Corp., Jupiter, Fla.), 1.35 g of S-Lec B Bx-5 polyvinylbutyral resin (Sekisui Chemical Co. Ltd.), 26 g of methyl ethyl ketone, and 13 g of toluene using a horizontal sand mill operating in recirculation mode for 8 hours. The resulting dispersion is then die coated onto unsubbed 2 mil (51 micrometer) thick polyethylene terephthalate (PET) film and dried at 80° C. for 10 minutes to form a charge generating layer having a thickness of 0.27 micrometer on the PET film.

The charge transport layer and the charge generating layer are laminated together at 140° C. using a Model 447 Matchprint™ Laminator (obtained commercially from Imation Corp., Oakdale, Minn.). After lamination, the 2 mil (51 micrometer) PET film is peeled off the surface of the charge generation layer to form the inverted dual layer organophotoreceptor.

C. Electrostatic Testing

Electrostatic testing of Compound (2) and Compound (3) can be performed and recorded on a QEA PDT-2000 instrument at ambient temperature. Charge-up is performed at 8 kV. Discharge is performed by exposing the photoreceptor to a 780 nm-filtered tungsten light source down a fiber optic cable. Each sample is exposed to 2 microjoules/cm$^2$ of energy for 0.05 seconds; the total exposure intensity is 20 microwatts/cm$^2$. After charge-up, the acceptance voltage ($V_{acc}$) is measured in volts. This value is recorded as $V_{acc}$ after one cycle. Following this initial charge-up, a one second dark decay followed before the sample is discharged with the 0.05 second light pulse of 2 microjoules/cm$^2$ at 780 nm, one second after which the decrease in voltage (Contrast) is measured in volts. Then the charge on the sample is further reduced by an eraser lamp. The final residual voltage ($V_{res}$) on the sample is measured in volts. $V_{acc}$ and $V_{res}$ are also measured after a total of 1000 cycles. In general, it is desirable to maximize $V_{acc}$ and to minimize $V_{res}$.

D. Ionization Potential Measurement

Samples for ionization potential (Ip) measurements were prepared by dissolving Compounds 2 and 14 independently in tetrahydrofuran. Each solution was hand-coated on an aluminized polyester substrate that was precision coated with a methylcellulose-based adhesion sub-layer to form a charge transport material (CTM) layer. The role of this sub-layer was to improve adhesion of the CTM layer, to retard crystallization of CTM, and to eliminate the electron photoemission from the Al layer through possible CTM layer defects. No photoemission was detected from the Al through the sub-layer at illumination with up to 6.4 eV quanta energy light. In addition, the adhesion sub-layer was conductive enough to avoid charge accumulation on it during measurement. The thickness of both the sub-layer and CTM layer was ~0.4 $\mu$m. No binder material was used with CTM in the preparation of the samples for Ip measurements.

The ionization potential was measured by the electron photoemission in air method similar to that described in "Ionization Potential of Organic Pigment Film by Atmospheric Photoelectron Emission Analysis", Electrophotography, 28, Nr. 4, p. 364. (1989) by E. Miyamoto, Y. Yamaguchi, and M. Yokoyama, which is hereby incorporated by reference. The samples were illuminated with monochromatic light from the quartz monochromator with a deuterium lamp source. The power of the incident light beam was 2–5·10$^{-8}$ W. The negative voltage of −300 V was supplied to the sample substrate. The counter-electrode with the 4.5×15 mm$^2$ slit for illumination was placed at 8 mm distance from the sample surface. The counter-electrode was connected to the input of the BK2-16 type electrometer, working in the open impute regime, for the photocurrent measurement. A 10$^{-15}$–10$^{-12}$ amp photocurrent was flowing in the circuit under illumination. The photocurrent, I, was strongly dependent on the incident light photon energy hv. The 1$^{0.5}$=f(hv) dependence was plotted. Usually the dependence of the square root of photocurrent on incident light quanta energy is well described by linear relationship near the threshold [see references "Ionization Potential of Organic Pigment Film by Atmospheric Photoelectron Emission Analysis", Electrophotography, 28, Nr. 4, p. 364. (1989) by E. Miyamoto, Y. Yamaguchi, and M. Yokoyama; and "Photoemission in Solids", Topics in Applied Physics, 26, 1–103 (1978) by M. Cordona and L. Ley]. The linear part of this dependence was extrapolated to the hv axis and Ip value was determined as the photon energy at the interception point. The ionization potential measurement has an error of ±0.03 eV. The ionization potential data are listed in Table 1.

E. Hole Mobility Measurement

Samples for charge carrier mobility measurements were prepared by dissolving Compounds 2 and 14 independently in tetrahydrofuran with a binder to form 10% solid solutions. The binder was polycarbonate Z 200 (commercially obtained from Mitsubishi Engineering Plastics, White Plains, N.Y.). The sample/binder ratio was 4:6 or 5:5. Each solution was coated on an aluminized polyester substrate to form a charge transport material (CTM) layer. The thickness of the CTM layer varied in the range of 5–10 $\mu$m.

The hole drift mobility was measured by a time of flight technique as described in "The discharge kinetics of negatively charged Se electrophotographic layers," Lithuanian Journal of Physics, 6, p. 569–576 (1966) by E. Montrimas, V. Gaidelis, and A. Pažėra, which is hereby incorporated by reference. Positive corona charging created electric field inside the CTM layer. The charge carriers were generated at the layer surface by illumination with pulses of nitrogen laser (pulse duration was 2 ns, wavelength 337 nm). The layer surface potential decreased as a result of pulse illumination was up to 1–5% of initial potential before illumination. The capacitance probe that was connected to the wide frequency band electrometer measured the speed of the surface potential dU/dt. The transit time $t_t$ was determined by the change (kink) in the curve of the dU/dt transient in linear or double logarithmic scale. The drift mobility was calculated by the formula $\mu = d^2/U_0 \cdot t_t$, where d is the layer thickness and $U_0$ is the surface potential at the moment of illumination.

Mobility values at electric field strength, E, of $6.4 \cdot 10^5$ V/cm are given in the Table 1. The mobility field dependencies may be approximated by the function $$\mu \sim e^{\alpha\sqrt{E}}$$

where α is parameter characterizing mobility field dependence.

TABLE 1

|  | $I_P$ eV | Charge carrier | Mobility (cm$^2$/Vs) | Remarks |
|---|---|---|---|---|
| Compound 5 | 5.64 | Holes | ~10$^{-6}$ | Signal dispersive |
| Comparative Example A* | 5.36 | Holes | 4.4.10$^{-6}$ | — |

Note:
*Comparative Example A is Compound (2) in U.S. Pat. No. 6,140,200.

The examples and disclosure are intended to represent non-limiting examples of the practice of the invention. Alternative materials for ancillary aspects of the invention (as opposed to the generic chemical structures that constitute the underlying basis of the invention) are within the discretion of the skilled artisan and may be varied within the scope of the invention. Times, temperatures and conditions of the process of using the imaging systems of the invention may likewise be varied within the practice of the invention. As alternative processes and materials are developed within the field of the invention, those materials would be used with the underlying materials of the invention. Other embodiments are within the following claims.

What is claimed is:

1. An organophotoreceptor comprising:

(a) a charge transport compound having the formula where
    $R_1$ and $R_2$ are, independently, a fluorenyl group;
    $R_3$ and $R_4$ are, independently, hydrogen, an alkyl group, an aryl group, or a heterocyclic group; and
    X is a sulfonyldiphenylene group;

(b) a charge generating compound; and (c) an electrically conductive substrate.

2. An organophotoreceptor according to claim 1 wherein said organophotoreceptor is in the form of a flexible belt.

3. The organophotoreceptor of claim 1 wherein the charge transport compound and the charge generating compound are present in a single layer.

4. The organophotoreceptor of claim 1 wherein the charge transport compound and the charge generating compound are each present in different adjacent layers.

5. An organophotoreceptor according to claim 1 comprising:

(a) a charge transport layer comprising said charge transport compound and a polymeric binder;

(b) a charge generating layer comprising said charge generating compound and a polymeric binder; and (c) said electrically conductive substrate.

6. The organophotoreceptor of claim 1 wherein the charge transport compound has a central nucleus of the formula:

where $R_5$ and $R_6$ are, independently, hydrogen, an alkyl group, or an aryl group.

7. The organophotoreceptor of claim 6 wherein the charge transport compound is selected from the group consisting of the following compounds:

8. An electrophotographic imaging apparatus comprising:
(a) a plurality of support rollers; and
(b) an organophotoreceptor in the form of a flexible belt threaded around said support rollers, said organophotoreceptor comprising:
  (i) a charge transport compound having the formula

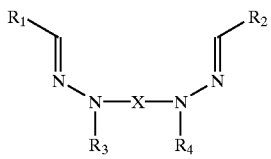

where
    $R_1$ and $R_2$ are, independently, a fluorenyl group;
    $R_3$ and $R_4$ are, independently, hydrogen, an alkyl group, an aryl group, or a heterocyclic group; and
    X is a sulfonyldiphenylene group;
  (ii) a charge generating compound; and
  (iii) an electrically conductive substrate.

9. An electrophotographic imaging process comprising:
(a) applying an electrical charge to a surface of an organophotoreceptor comprising:
  (i) a charge transport compound having the formula

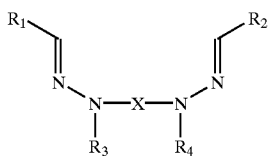

where
    $R_1$ and $R_2$ are, independently, a fluorenyl group;
    $R_3$ and $R_4$ are, independently, hydrogen, an alkyl group, an aryl group, or a heterocyclic group; and
    X is a sulfonyldiphenylene group;
  (ii) a charge generating compound; and
  (iii) an electrically conductive substrate;

(b) imagewise exposing said surface of said organophotoreceptor to radiation to dissipate charge in selected areas and thereby form a pattern of charged and uncharged areas on said surface;
(c) contacting said surface with a liquid toner comprising a dispersion of colorant particles in an organic liquid to create a toned image; and
(d) transferring said toned image to a substrate.

10. A charge transport compound having the formula

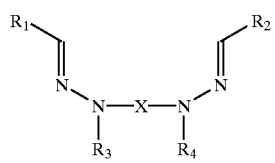

where
  $R_1$ and $R_2$ are, independently, a fluorenyl group;
  $R_3$ and $R_4$ are, independently, hydrogen, an alkyl group, an aryl group, or a heterocyclic group; and
  X is a sulfonyldiphenylene group.

11. The charge transport compound of claim 10 having a central nucleus of the formula:

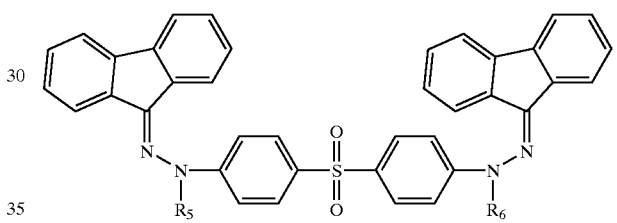

where $R_5$ and $R_6$ are, independently, hydrogen, an alkyl group, or an aryl group.

12. The charge transport compound of claim 11 selecting from the group consisting of the following compounds:

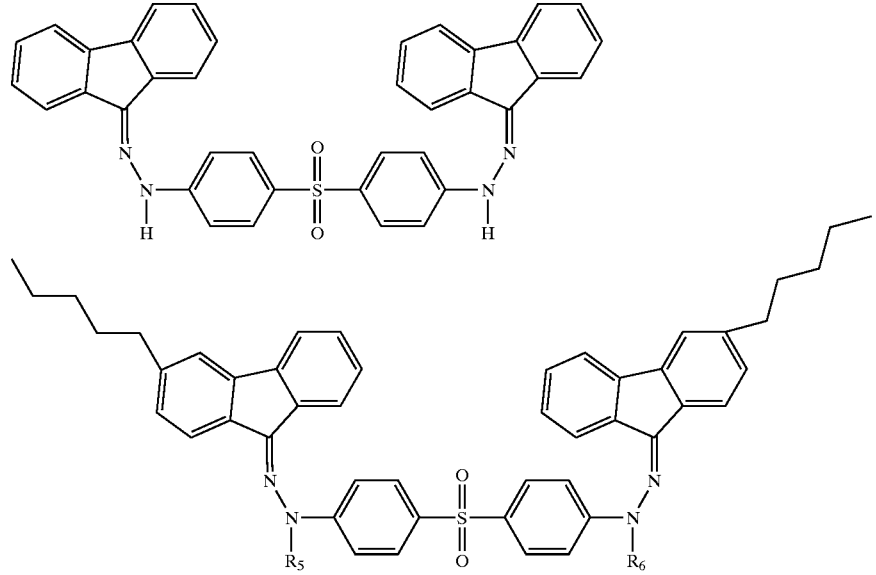

* * * * *

UNITED STATES PATENT AND TRADEMARK OFFICE
CERTIFICATE OF CORRECTION

PATENT NO. : 6,696,209 B2  
DATED : February 24, 2004  
INVENTOR(S) : Kam W. Law et al.

Page 1 of 1

It is certified that error appears in the above-identified patent and that said Letters Patent is hereby corrected as shown below:

Column 23,
Line 58, please delete the word "tt" and insert in its place -- $t_t$. --

Signed and Sealed this

Seventh Day of June, 2005

JON W. DUDAS
*Director of the United States Patent and Trademark Office*